United States Patent [19]

Thorwart et al.

[11] Patent Number: 4,908,364

[45] Date of Patent: Mar. 13, 1990

[54] SUBSTITUTED 3-PHENYL-7H-THIAZOL[3,2-b][1,2,4]-TRIAZIN-7-ONES

[75] Inventors: Werner Thorwart, Hochheim am Main; Ulrich Gebert, Kelkheim; Rudolf Schleyerbach, Hofheim am Taunus; Robert R. Bartlett, Darmstadt, all of Fed. Rep. of Germany

[73] Assignee: Hoechst Aktiengesellschaft, Frankfurt am Main, Fed. Rep. of Germany

[21] Appl. No.: 149,603

[22] Filed: Jan. 28, 1988

[30] Foreign Application Priority Data

Jan. 30, 1987 [DE] Fed. Rep. of Germany ....... 3702758

[51] Int. Cl.⁴ .................... A61K 31/53; A61K 31/55; C07D 513/04; C07D 417/06
[52] U.S. Cl. .................................. 514/243; 544/184; 544/58.6; 544/112; 540/599; 540/575; 514/212; 514/233.2; 514/228.5; 514/218
[58] Field of Search ...................... 544/184, 58.6, 112; 514/243, 233.2, 228.5, 218; 540/599, 575

[56] References Cited

U.S. PATENT DOCUMENTS 4,522,944 6/1985 Doria et al. .................... 514/222

FOREIGN PATENT DOCUMENTS 3146300 8/1983 Fed. Rep. of Germany .
3346223 6/1984 Fed. Rep. of Germany .

OTHER PUBLICATIONS

K. Brune, Eur. J. Rheumatol. Inflam. 5, pp. 335-349, 1982.
E. A. Ibrahim et al., Pharmazie 34, H.7, pp. 392-394, 1979.
F. Arndt et al., Liebigs Ann. Chem., 1984, pp. 1302-1307.
Doleschall et al., Chem. Abstr. 68:29682p, 1968.
Hornyak et al., Chem. Abstr. 69:96679b, 1968.
Doleschall et al., Chem. Abstr. 85:5599s, 1976.
Kallias et al., J. Heterocyclic Chem. 17, 1980, 1045-1047.
Giannola et al., J. Chem. Soc. Perkin Trans. I, 1984, 2707-2710.
Busby et al., J. C. S. Perkin II, pp. 890-899, 1980.
Bulka et al., Z. Chem., 15, No. 12, p. 482, 1975.
G. Toth et al., Chem. Ber. 110, pp. 1492-1496, 1977.
Ibrahim et al., Chem. Abs., 92, No. 9, 92:76459f, 1980.
M. Mizutani, Pat. Abs. of Japan (1984), 59-21672.
Chem. Abs. 104:50789a, 1986.
Van der Goot et al., Chem. Abs. 90:114920p, 1979.

Primary Examiner—John M. Ford
Attorney, Agent, or Firm—Finnegan, Henderson, Farabow, Garrett and Dunner

[57] ABSTRACT

Novel substituted 3-phenyl-7H-thiazolo[3,2-b][1,2,4]-triazin-7-ones of the formula I are disclosed

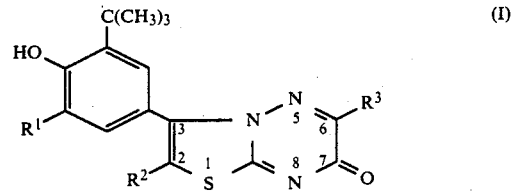

in which R¹, R² and R³ have the meaning recited in the specification. The compounds are suitable for prevention and treatment of inflammatory disorders.

14 Claims, No Drawings

SUBSTITUTED 3-PHENYL-7H-THIAZOL[3,2-b][1,2,4]-TRIAZIN-7-ONES

DESCRIPTION

The present invention relates to novel polysubstituted 3-phenyl-7H-thiazolo[3,2-b][1,2,4]triazin-7-ones, a process for the preparation thereof and the use thereof as active compounds in medicaments, in particular for the treatment of rheumatic disorders; in addition, the invention also relates to some intermediates formed in the preparation of the abovementioned compounds.

The non-steroidal antiphlogistics preferably employed hitherto in rheumatherapy are almost exclusively relatively strong cyclooxygenase inhibitors, which inhibit endogenic degradation of arachidonic acid into inflammation- and pain-promoting prostaglandins. However, a number of serious side-effects, such as gastrointestinal complaints, kidney dysfunctions and allergic reactions (e.g. skin allergies and asthmatic attacks), which frequently cause termination of the therapy, in particular in the case of the long-term treatment which is usually necessary, are causally associated with excessive inhibition of cyclooxygenase activity (cf. K. Brune, Eur. J. Rheumatol. Inflam. 5, 335–349, 1982).

A further disadvantage of these classical non-steroidal antiphlogistics which is causally connected with the mechanism of action described is that, although they permit elimination or alleviation of pain, inflammation and swelling symptoms, they do not affect the immunopathological processes underlying inflammatory rheumatic disorders and are therefore not capable of halting the advanced course of the disorder.

There is thus an urgent requirement for therapeutically useful antirheumatics which, due to a more favorable action profile, differ advantageously from the known non-steroidal antiphlogistics through better tolerances on the one hand and a more causal engagement in the rheumatic pathological process on the other hand. Promising starting points for such medicaments are pharmaceuticals which engage to an increased extent in the alternative route of arachidonic degradation, for example by inhibiting 5-lipoxygenase and thus suppressing excessive formation of proinflammatory leucotrienes, deactivating highly-reactive oxygen radicals which, as inflammation mediators, perpetually maintain cell and tissue destruction in the inflammatory rheumatic joints and/or restoring the impaired immune system and thus opening up the possibility of using medicaments to treat rheumatic disorders more causally.

Surprisingly, it has now been found that, by introducing certain 3-substituted 5-tert.-butyl-4-hydroxyphenyl radicals into the 3-position of optionally 2- and/or 6-substituted 7H-thiazolo[3,2-b][1,2,4]triazin-7-ones, novel compounds are obtained which, due to their pharmacological properties, meet the demands set above and accordingly are highly suitable for treatment of rheumatic disorders.

In contrast to the known non-steroidal antiphlogistics, the compounds, which are also extremely well tolerated gastrally, inhibit the arachidonic acid-degrading enzyme 5-lipoxygenase, while an effect on cyclooxygenase cannot be detected. The ability of the compounds to deactivate oxygen radicals is apparent, for example, in the model of $^{(R)}$Adriamycin (Messrs. Farmitalia) induced inflammation and through the inhibition of lipid peroxidation.

In addition, they engage advantageously in the disturbed immune system, as can be demonstrated by suppressing the Arthus reaction and by normalization of the suppressed immune activity in the pathological models of arthritis induced by means of Freund's adjuvant or type II collagen.

Some 7H-thiazolo[3,2-b][1,2,4]triazin-7-ones are already known from the literature. Thus, F. Soliman et al. prepared 6-(3-iodostryl)-3-methyl-7H-thiazolo[3,2-b][1,2,4]-triazin-5-one when searching for compounds having an antineoplastic activity, but did not report on its pharmacological properties (Pharmazie 34 (1979), pp. 392–394). The same ring system having an alkyl or phenyl radical in the 6-position has been constructed by W. Klose et al. (Liebigs Ann. Chem. 1984, pp. 1302–1307); these compounds are said to have a herbicidal action. Finally, 3,6-diphenyl-7H-thiazolo[3,2-b][1,2,4]triazin-7-one is described in German Offenlegungsschrift 3,146,300, in addition to a whole series of partially hydrogenated 7H-thiazolo[3,2,-b][1,2,4]triazin-7-ones, and the corresponding 3-methyl-6-phenyl derivative is mentioned, which is likewise said to have a herbicidal activity.

By contrast, the present invention relates to novel 7H-thiazolo[3,2-b][1,2,4]triazin-7-ones which carry a 3-substituted 5-tert.-butyl-4-hydroxyphenyl group in the 3-position and, if appropriate, further substituents in the 2-and/or 6-position, the introduction of a phenyl radical into the 6-position of the bicyclic system leading, however, to complete loss of action. Due to their abovementioned pharmacological properties, the compounds according to the invention are suitable for use in medicaments, in particular in those which are indicated in inflammatory rheumatic disorders.

The invention thus relates to substituted 3-phenyl-7H-thiazolo[3,2-b][1,2,4]triazin-7-ones of the general formula I in which

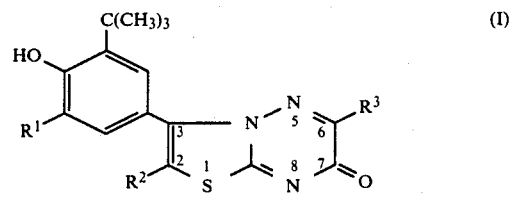

R¹ denotes a straight-chain or branched alkyl group having 1 to 4 carbon atoms, hydroxymethyl or an aminomethyl group of the formula II

R² denotes a hydrogen atom or an alkyl radical having 1 to 3 carbon atoms, and
R³ denotes a hydrogen atom, a straight-chain or branched alkyl group having 1 to 4 carbon atoms, hydroxymethyl or an aminomethyl group of the formula II, where
R⁴ and R⁵ are identical or different and denote a hydrogen atom or a straight-chain or branched alkyl radical having 1 to 4 carbon atoms, or the two radicals, together with the nitrogen atom to which they are bound, form a 5- to 7-membered saturated ring having 4 to 6 carbon atoms or having 4 or 5 carbon atoms and additionally having a further heteroatom in the form of O, S or NR$^6$, and R$^6$ denotes hydrogen or (C$_1$–C$_4$)-alkyl,
and the physiologically acceptable acid-addition salts of the compounds having the structural element of the formula II in the positions of R$^1$ and/or R$^3$.

If R$^4$ and R$^5$, together with the nitrogen atom to which they are bound, form a saturated ring having 4 or 5 carbon atoms and additionally having a further heteroatom, the heteroatoms must be separated from one another by at least 1 carbon atom.

Preferred compounds of the formula I here are those in which either R$^1$ denotes a tert.butyl radical or an aminomethyl group of the formula II or R$^2$ and R$^3$, independently of one another, represent hydrogen or methyl. In addition, compounds of the formula I which should be particularly emphasized are those in which R$^1$ denotes a tert.-butyl group and simultaneously R$^2$ and R$^3$, independently of one another, represent hydrogen or methyl, such as, for example, 3-(3,5-di-tert.butyl-4-hydroxyphenyl)7H-thiazolo[3,2-b][1,2,4]triazin-7-one.

Suitable alkyl radicals for the R$^1$ and R$^3$ to R$^6$ groups are methyl, ethyl, n-propyl, isopropyl, n-butyl, isobutyl, sec.butyl and tert.butyl, and for the R$^2$ groups are methyl, ethyl, n-propyl and isopropyl. Suitable cyclic aminomethyl groups for the structural elements of the formula II are pyrrolidino, piperidino, hexamethyleneimino, morpholino, thiomorpholino and piperazino and homopiperazinomethyl which are both optionally alkylated on the second nitrogen atom.

The invention furthermore relates to a process for the preparation of the novel 7H-thiazolo[3,2-b][1,2,4]triazin-7-ones.

One embodiment (a) comprises, for example, reacting 3-mercapto-2H-1,2,4-triazin-5-ones of the formula III

(III)

in which R$^3$ has the abovementioned meaning, with 2-halo-1-phenylalkanones of the formula IV

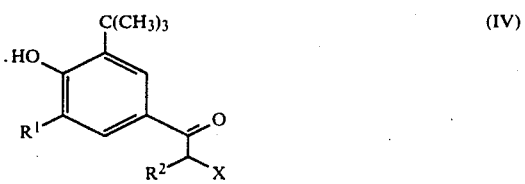

(IV)

in which R$^1$ denotes the above defined alklyl group, R$^2$ has the abovementioned meaning and X represents a halogen atom, preferably chlorine or bromine, to give the corresponding compounds of the formula I according to the invention.

Another embodiment (b) comprises reacting compounds of the formula III with a compound of the formula IV (where R$^1$=(C$_1$–C$_4$)-alkyl) under basic conditions to give, initially, S-alkylated 2H-1,2,4-triazin-5-ones of the formula V

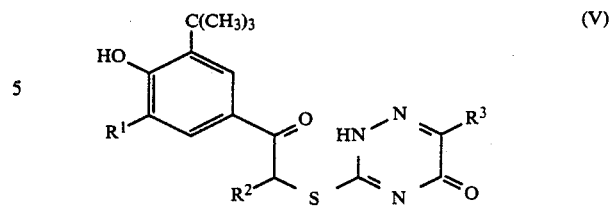

(V)

and converting the latter into the corresponding compounds of the formula I according to the invention through dehydration; the intermediates of the formula V are novel compounds.

A further embodiment (c) comprises reacting 2-halo-1-phenyl alkanones of the formula IV (where R$^1$=(C$_1$–C$_4$)-alkyl) initially with a thiosemicarbazide to give the corresponding—likewise novel—2-amino-6H-1,3,4-thiadiazines of the formula VI

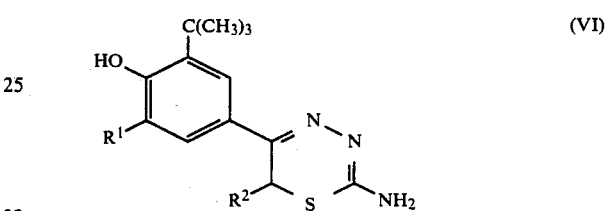

(VI)

and rearranging the latter under acid conditions into 3-amino-2-imino-2,3-dihydrothiazoles of the formula VII

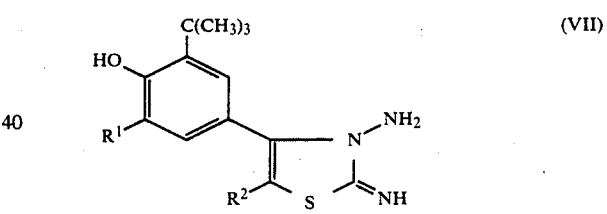

(VII)

which are subsequently cyclocondensed with α-ketocarboxylic acids, or alkyl esters thereof, of the formula VIII

(VIII)

in which R$^3$ denotes a hydrogen atom, a straight-chain or branched alkyl group having 1 to 4 carbon atoms or a hydroxymethyl group, and R$^7$ denotes a hydrogen atom or an alkyl radical having 1 to 3 carbon atoms, to give the relevant compounds of the formula I according to the invention.

A likewise practicable embodiment (d) comprises, starting from compounds of the formula I according to the invention which carry a hydroxymethyl radical in the position of R$^1$ and/or R$^3$, initially either replacing the hydroxyl group(s) of the latter by halogen or converting the hydroxyl group(s) into an activated sulfonate or phosphate, and subsequently reacting the product with amines of the formula IX

(IX)

in which $R^4$ and $R^5$ have the abovementioned meaning, to give compounds of the formula I according to the invention having the structural element of the formula II in the position of $R^1$ and/or $R^3$, these aminomethyl compounds either being isolated in free form or converted into physiologically acceptable addition salts by means of suitable acids.

A further embodiment (e), which is suitable for the preparation of compounds of the formula I having the structural feature of the formula II or having the hydroxymethyl radical in the position of $R^1$, comprises, finally, reacting compounds of the formula I in which $R^1$ represents hydrogen with formaldehyde in order to introduce the hydroxymethyl radical, reacting the product of this reaction with the appropriate amines of the formula IX, in the presence of formaldehyde, in order to introduce N-substituted aminomethyl groups of the formula II in which $R^4$ and $R^5$ do not, simultaneously represent hydrogen, or in order to introduce the unsubstituted aminomethyl radical ($R^4 = R^5 = H$), initially condensing these products with N-hydroxymethylacetamides of the formula X

 (X)

in which $R^8$ represents trifluoromethyl, trichloromethyl or chloromethyl, under acidic conditions and with elimination of water, and subsequently eliminating the acyl radical $R^8$—CO— hydrolytically, the aminomethyl compounds thus obtained either being isolated in free form or converted into physiologically acceptable addition salts by means of suitable acids.

Suitable for the preparation of these acid-addition salts are, for example, mineral acids, such as sulfuric acid or phosphoric acid, or hydrohalic acids, in particular hydrobromic acid and hydrochloric acid, and also organic acids, such as monobasic to tribasic carboxylic acids, for example acetic acid, lactic acid, maleic acid, fumaric acid, oxalic acid, tartaric acid, citric acid or other tolerated acids, such as sulfonic acids (benzenesulfonic acid, 4-toluenesulfonic acid, methanesulfonic acid, trifluoromethylsulfonic acid, cyclohexylamidosulfonic acid, etc.).

The 3-mercapto-2H-1,2,4-triazin-5-ones of the formula III used as starting materials for the process according to the invention are known (H. Neunhoeffer and P. L. Wiley in A. Weisberger and E. C. Taylor, The Chemistry of Heterocyclic Compounds, Wiley-Interscience, New York, Vol. 33 (1978) pp. 430–465) or can be prepared in an analogous fashion.

The 2-halo-1-phenylalkanones of the formula IV which are likewise used as starting materials are also known from the literature or can easily be prepared, for example from 1-(3-alkyl-5tert.butyl-4-hydroxyphenyl)-alkanones through reaction with a suitable halogenating agent by the methods described in Houben-Weyl Vol. V/4 pp. 171–189 (1960).

Suitable compounds IV which may be mentioned are, for example, 2-bromo-1-(3,5-di-tert.butyl-4-hydroxyphenyl)-ethanone and 2-bromo-1-(3-methyl-5-tert.butyl-4-hydroxyphenyl)-ethanone, which can be prepared by halogenation of the correspondingly substituted 1-phenylalkanones using elemental bromine or using copper(II) bromide by a process of L. C. King and K. G. Ostrum, J. Org. Chem. 29 (1964) pp. 3459–3461.

In order to obtain the compounds of the formula IV in which X represents a chlorine atom, sulfuryl chloride, which is preferably reacted with the appropriate 1-phenylalkanones at temperatures between about 10° and 30° C. in the presence of inert solvents, such as, for example, methylene chloride or chloroform, is especially suitable. A further preparation process comprises Friedel-Crafts acylation of 2-alkyl-6-tert.butylphenols, preferably using chloroacetyl chloride in the presence of Lewis acids, such as, for example, aluminum chloride or boron trifluoride.

In the reaction of 3-mercapto-2H-1,2,4-triazin-5-ones III with 2-halo-1-phenylalkanones IV in accordance with procedure (a), equimolar amounts of the reactants are usually used in a distributing agent or solvent. Suitable as such are, above all, polar solvents, for example lower aliphatic carboxylic acids, such as formic acid or acetic acid, or alcohols, such as methanol, ethanone, the various propanols or butanols. However, ethylene glycol and the ethers thereof, ethyl acetate, acetone, butan-2-one, dimethylformamide or acetonitrile, and also mixtures of the solvents mentioned or mixtures thereof with water, can also be used. The reaction temperatures are generally between about 20° C. and the boiling point of the particular reaction medium used. The reaction is preferably carried out in acetic acid between about 70° and 100° C., the reaction times generally being between less than one hour and about 6 hours.

The S-alkylated 2H-1,2,4-triazin-5-ones of the formula V required as intermediates in process variant (b) can be prepared by reacting 3-mercapto-2H-1,2,4-triazin-5-ones of the formula III, expediently with an equimolar amount of a 2-halo-1-phenylalkanone of the formula IV in the presence of a basic agent, such as an alkali metal hydroxide, carbonate, hydride or alcoholate or an alkaline-earth metal hydroxide, carbonate, hydride or alcoholate, or an organic base, for example a trialkylamine, such as triethylamine or tributylamine. The reaction is preferably carried out in a distributing agent or solvent, or mixtures thereof, which are indifferent to the reactants. Suitable as such are, for example, water, alcohols, such as methanol, ethanone, the various propanols and butanols, ethers, such as diethyl ether, diisopropyl ether, tetrahydrofuran and dioxane, nitriles, such as acetonitrile, ketones, such as acetone and butanone, and also dimethylformamide, dimethylacetamide and dimethyl sulfoxide. The reaction is generally carried out between about 0° and the boiling point of the reaction medium, preferably between about 30° and 90° C., reaction times of, on average, one to several hours being required.

The subsequent dehydration of the compounds V with cyclization to form the compounds of the formula I according to the invention is preferably carried out in the presence of an acid, such as hydrochloric acid, hydrobromic acid, sulfuric acid, p-toluenesulfonic acid, polyphosphoric acid or acetic acid in an ether, such as diisopropyl ether, tetrahydrofuran and dioxane, or an alcohol, such as methanol, ethanone, or propanol, or mixtures thereof with water, at temperatures from about 0° to 80° C., in particular from about 10° to 40° C., and reaction times from about one hour up to several days.

Procedure (c) proceeds via 2-amino-6H-1,3,4-thiadiazines of the formula VI as intermediates, which can easily be prepared from 2-halo-1-phenylalkanones of the formula IV and thiosemicarbazide by methods which are known from the literature. The rearrangement of these intermediates into the corresponding 3-amino-2-imino-2,3-dihydrothiazols of the formula VII preferably takes place in an acidic medium, such as, for example, in hydrochloric acid, hydrobromic acid, sulfuric acid or acetic acid, and mixtures thereof or mixtures thereof with water.

The subsequent cyclocondensation to give compounds of the formula I is generally carried out without intermediate isolation of the 3-amino-2-imino-2,3-dihydrothiazols VII formed as intermediates, by adding to the reaction mixture an α-ketocarboxylic acid, or an alkyl ester thereof, of the formula VIII, such as, for example, glyoxylic acid or pyruvic acid, or the methyl or ethyl esters thereof, in up to twice the equimolar amount. The temperatures during this reaction are preferably between about 50° C. and the boiling point of the particular reaction medium used, while the reaction times may generally be from about 5 to about 30 hours.

The possible conversion of the compounds of the formula I according to the invention which carry a hydroxymethyl radical in the position of $R^1$ and/or $R^3$ into the aminomethyl compound of the formula I corresponding to embodiment (d) is carried out in the conventional fashion. Thus, the hydroxyl group can be activated, for example, by reaction with halogenating agents, such as thionyl chloride, phosphorus trichloride or phosphorus tribromide, to give the halomethyl compounds, or by esterification, for example using methanesulfonyl chloride or toluene-4-sulfonyl chloride. The subsequent condensation reaction with the amines of the formula IX is advantageously carried out in the presence of at least twice the molar amount of the particular amine employed per derivatized hydroxymethyl group; it is also possible to use equivalent amounts of both reactants, but the addition of an acid-binding agent, for example an alkali metal hydroxide or carbonate or an alkaline-earth metal hydroxide or carbonate, or alternatively an organic base, such as triethylamine or pyridine, in at least the stoichiometric amount is then advisable. The reaction is expediently carried out in a solvent or distributing agent which is inert towards the reactants. Suitable for this purpose are, for example, alcohols, such as methanol, ethanone, isopropanol, n-propanol, the various butanols, and mixtures thereof, of alternatively mixtures thereof with ethers, such as tetrahydrofuran and dioxane, or hydrocarbons, such as benzene, toluene and xylene, and also aprotic solvents, such as pyridine, dimethylformamide, dimethylacetamide, dimethyl sulfoxide and hexamethylphosphoric triamide. The reaction is generally carried out at temperatures between about 0° C. and the boiling point of the particular solvent, preferably between about 20° and 100° C., it being possible for the reaction time to be up to several hours.

In order to introduce the aminomethyl groups of the formula II into the compounds of the formula I in which $R^1$ represents hydrogen in the fashion of procedure (e), the Mannich reaction, which is sufficiently known from the literature (e.g. Houben-Weyl, Vol. XI/1 (1957), pp. 755-763), are advantageously used in the case of the reactions with primary and, in particular, secondary amines of the formula IX. The formaldehyde which participates in the reaction can be employed either in monomeric form as an aqueous solution or in polymeric form as a solid (for example paraformaldehyde). In general, the reaction is carried out using 4 to 10 times the molar amount of formaldehyde and an up to 40-fold molar excess of the particular amine, which can also be reacted in the form of its hydrohalides. The preferred reaction medium is water or alcohols, such as methanol, ethanone or propanol, or mixtures thereof. The reaction is preferably carried out at temperatures between about 20° and 100° C., reaction times from one hour to several days being required.

The condensation with the N-hydroxymethylacetamides of the formula X is the preferred way of introducing the aminomethyl radical which is unsubstituted on the nitrogen atom. Suitable condensation agents are acids, such as, for example, methanesulfonic acid or mixtures of concentrated sulfuric acid and glacial acetic acid, which can simultaneously serve as the reaction medium, the reaction generally proceeding between about 0° C. and room temperature and being complete within 30 minutes to 6 hours. The elimination of the acyl radical from the N-acylated aminomethyl compounds primarily formed takes place by acid hydrolysis by standard methods which are sufficiently known to those skilled in the art, it having proven particularly successful to work in aqueous hydrochloric acid, hydrobromic acid or sulfuric acid at elevated temperature, preferably at the boiling point of the particular reaction medium.

The 7H-thiazolo[3,2-b][1,2,4]triazin-7-ones of the formula I and the corresponding acid-addition salts thereof are particularly suitable, due to their valuable pharmacological properties and, at the same time, their excellent tolerance, for use as active compounds in medi-caments, in particular in those for treatment of inflammatory rheumatic disorders. They can be administered either alone, for example in the form of microcapsules, in mixtures with one another or in combination with suit-able adjuvants and/or excipients.

The invention thus also relates to medicaments which comprise at least one compound of the formula I and/or at least one of the corresponding acid-addition salts thereof or contain at least one of these active compounds in addition to pharmaceutically suitable and physiologically acceptable excipients, diluents and/or other adjuvants.

The medicaments according to the invention can be administered orally, topically, rectally or, if appropriate, also parenterally, oral administration being preferred.

Suitable solid or liquid galenic formulations are, for example, granules, powders, coated tablets, tablets, (micro)capsules, suppositories, syrups, elixirs, suspensions, emulsions, drops or injectable solutions, and also preparations having a protracted release of active compound, in whose preparation adjuvants, such as excipients, disintegrants, binders, coating agents, swelling agents, glidants or lubricants, flavors, sweeteners or solubilizers are usually used. Magnesium carbonate, titanium dioxide, lactose, mannitol and other sugars, talc, lactalbumin, gelatin, starch, cellulose and derivatives thereof, animal and vegetable oils, polyethylene glycols and solvents, such as, for example, sterile water and monohydric or polyhydric alcohols, for example glycerol, may be mentioned as examples of frequently used adjuvants.

The pharmaceutical preparations are preferably produced and administered in dosage units, each unit containing as active component a certain dose of at least one compound of the formula I and/or at least one corresponding acid-addition salt. In the case of solid dosage units, such as tablets, capsules, coated tablets or suppositories, this dose can be up to about 800 mg, but preferably about 100 to 500 mg.

For the treatment of an adult patient suffering from inflammatory rheumatic disorders, daily doses from about 100 to 2,000 mg of active compound, preferably about 300 to 1,000 mg are indicated in the case of oral administration—depending on the activity in humans of the compounds of the formula I and/or the corresponding acid-addition salts. Under certain circumstances, however, higher or lower daily doses may be appropriate. Administration of the daily dose can take place either by a single administration in the form of a single dosage unit or several smaller dosage units, or by multiple administration of divided doses at certain intervals.

Finally, the compounds of the formula I and the corresponding acid-addition salts can also be formulated, during the production of the abovementioned galenic formulations, together with other suitable active compounds, for example antiuricopathics, thrombocyte-aggregation inhibitors, analgesics and other steroidal or non-steroidal antiphlogistics.

The structure of all the compounds described below has been confirmed by elemental analysis and IR and $^1$H NMR spectra. The compounds of the formula I prepared in accordance with Examples 1 to 5 and 12 and 13 below and those prepared in analogous fashion are collated in Table 1.

EXAMPLE 1

3-(3,5-Di-tert.butyl-4-hydroxyphenyl)-7H-thiazolo[3,2-b][1,2,4]triazin-7-one by procedure (a)

(a₁)  2-Bromo-1-(3,5-di-tert.butyl-4-hydroxyphenyl)-ethanone

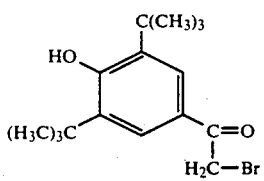

206 g (0.83 mol) of 1-(3,5-di-tert.butyl-4-hydroxyphenyl)-ethanone were dissolved in 415 ml of methylene chloride while stirring, the mixture was heated to boiling, and 144 g (0.9 mol) of bromine were added dropwise over the course of 30 minutes. The mixture was then refluxed for a further 2 hours and cooled, 400 ml of water were added, and the organic phase was separated off and dried over sodium sulfate. After the solvent had been removed under reduced pressure, the solid crude product obtained was recrystallized from 540 ml of methylcyclohexane.

Yield: 191 g (67% of theory). Melting point: 105°–108° C. $C_{16}H_{23}BrO_2$ (MW=327.3).

(a₂)    3-(3,5-Di-tert.butyl-4-hydroxyphenyl)-7H-thiazolo[3,2-b)][1,2,4]triazin-7-one

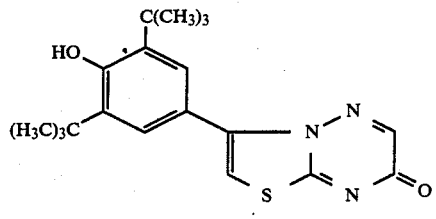

197 g (0.6 mol) of 2-bromo-1-(3,5-di-tert.butyl-4-hydroxyphenyl)-ethanone from step (a₁) and 80 g (0.62 mol) of 3-mercapto-2H-1,2,4-triazin-5-one were stirred for 4 hours at 90° C. in 700 ml of glacial acetic acid. The reaction mixture was then allowed to cool slowly, and the crystalline precipitate formed was filtered off under suction, subsequently washed with water and then washed by stirring at a maximum 90° C. for 30 minutes in 1,000 ml of water. The recrystallization of the batch of crystals, which was still moist with water, was carried out from 7,000 ml of ethanol.

Yield: 171.6 g (80% of theory). Melting point: 257° C. (decomp.). $C_{19}H_{23}N_3O_2S$ (MW=357.5).

Analysis: Calculated: C 63.84%; H 6.49%; N 11.75%; S 8.99%. Found: C 63.55%; H 6.44%; N 12.03%; S 9.00%.

by procedure (b)

(b₁)  3-[(3,5-Di-tert.butyl-4-hydroxyphenacyl)-thio]-2H-1,2,4-triazin-5-one

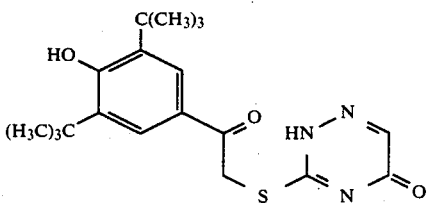

5.3 g (0.05 mol) of sodium carbonate were added to a suspension of 12.9 g (0.1 mol) of 3-mercapto-2H-1,2,4-triazin-5-one in 250 ml of water, the mixture was stirred for 30 minutes, a solution of 32.7 g (0.1 mol) of 2-bromo-1-(3,5-di-tert.butyl-4-hydroxyphenyl)-ethanone in 250 ml of methanol was then added dropwise, and the reaction mixture was kept at 75° C. for 1 hour. After cooling, the precipitate produced was filtered off and recrystallized from ethyl acetate.

Yield: 26.6 g (71% of theory). Melting point: 209°–211° C. $C_{19}H_{25}N_3O_3S$ (MW=375.5).

Analysis: Calculated: C 60.78%; H 6.71%; N 11.19%; S 8.54%. Found: C 60.45%; H 6.82%; N 11.06%; S 8.68%.

(b₂)      3-(3,5-Di-tert.butyl-4-hydroxyphenyl)-7H-thiazolo[3,2-b][1,2,4]triazin-7-one 3.7 g (0.01 mol) of 3-[(3,5-di-tert.butyl-4-hydroxyphenacyl)-thio]-2H-1,2,4-triazin-5-one from step (b₁) were stirred for 36 hours at room temperature in a mixture of 60 ml of tetrahydrofuran and 50 ml of 2N hydrochloric acid. The cyclocondensation product which slowly precipitated out was filtered off and recrystalized once to three times from tetrachlorofuran/ethanol (3:2).

Yield: 1.5 g (42% theory). Melting point: 256°–257° C. (decomp.). $C_{19}H_{23}N_3O_2S$ (MW=357.5).

Analytical and spectroscopic data confirmed the identity of the product obtained as the compound prepared by procedure (a).

by procedure (c)

(c₁) 2-Amino-5-(3,5-di-tert.butyl-4-hydroxyphenyl)-6H-1,3,4-thiadiazine hydrobromide

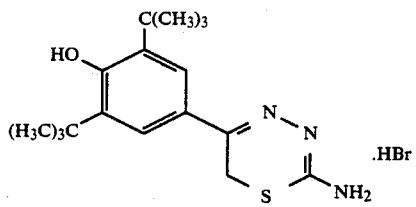

A solution of 32.7 g (0.1 mol) of 2-bromo-1-(3,5-di-tert.butyl-4-hydroxyphenyl)-ethanone (Example 1a₁) and 9.1 g (0.1 mol) of thiosemicarbazide in 250 ml of glacial acetic acid was stirred for 1 hour at room temperature, and the deposited precipitate was filtered off and dissolved in 500 ml of hot ethanol. After cooling, the crystals were filtered off under suction, washed repeatedly with ethyl acetate and dried in vacuo.

Yield: 27.2 g (68% of theory). Melting point: 255°–257° C. $C_{17}H_{26}BrN_3OS$ (MW=400.4).

Analysis: Calculated: C 51.00%; H 6.55%; Br 19.96%; N 10.49%; S 8.01%. Found: C 50.71%; H 6.52%; Br 19.92%; N 10.46%; S 8.17%.

(c₂) 3-(3,5-Di-tert.butyl-4-hydroxyphenyl)-7H-thiazolo[3,2-b][1,2,4]triazin-7-one 4.8 g (0.05 mol) of glyoxylic acid monohydrate in 75 ml of water were added dropwise to a solution of 10.0 g (0.025 mol) of 2-amino-5-(3,5-di-tert.butyl-4-hydroxyphenyl)-6H-1,3,4-thiadiazine hydrobromide from step (c₁) in 250 ml of glacial acetic acid and 25 ml of 4N hydrochloric acid at 80° C. After the mixture had been stirred at 80° C. for 20 hours, it was evaporated under reduced pressure. It was advantageously possible to purify the solid residue by column chromatography on silica gel using methylene chloride/methanol (25:1) as the eluent and subsequent recrystallization from ethanol, and, from analytical and spectroscopic investigations, the product proved to be identical to that prepared by procedures (a) and (b).

Yield: 3.9 g (42% of theory). Melting point: 255°–256° C. (decomp.). $C_{19}H_{23}N_3O_2S$ (MW=375.5).

EXAMPLE 2

3-(3-tert.butyl-5-methyl-4-hydroxyphenyl)-7H-thiazolo[3,2-b][1,2,4]triazin-7-one (a₁) 2-Bromo-1-(3-tert.butyl-5-methyl-4-hydroxyphenyl)-ethanone

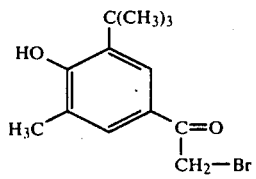

A solution of 82.5 g (0.4 mol) of 1-(3-tert.butyl-5-methyl-4-hydroxyphenyl)-ethanone in 360 ml of chloroform was added dropwise while stirring to a suspension, heated to boiling, of 179 g (0.8 mol) of copper(II) bromide in 360 ml of ethyl acetate. The mixture was subsequently refluxed for 4 hours until the evolution of hydrogen bromide was complete. After the mixture had been cooled to room temperature, the copper salts were filtered off under suction, the filter residue was washed repeatedly with ethyl acetate, the filtrate was evaporated under reduced pressure, and the solid residue was recrystallized from cyclohexane.

Yield: 81.9 g (72% of theory). Melting point: 90°–92° C. $C_{13}H_{17}BrO_2$ (MW=285.2).

(a₂) 3-(3-Tert.butyl-5-methyl-4-hydroxyphenyl)-7H-thiazolo[3,2-b][1,2,4]triazin-7-one

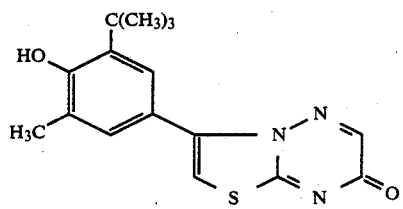

A solution of 28.5 g (0.1 mol) of 2-bromo-1-(3-tert.butyl-5-methyl-4-hydroxyphenyl)-ethanone from step (a₁) and 12.9 g (0.1 mol) of 3-mercapto-2H-1,2,4-triazin-5-one was refluxed for 8 hours in 250 ml of ethanol. After the solvent had been removed in vacuo, the solid residue was dissolved in 200 ml of boiling ethyl acetate and filtered while hot. On concentration of the filtrate, colorless crystals were produced which were again recrystallized from isopropanol.

Yield: 18.9 g (61% of theory). Melting point: 225°–226° C. (decomp.). $C_{16}H_{17}N_3O_2S$ (MW=315.4).

Analysis: Calculated: C 59.23%; H 8.08%; N 12.95%; S 9.88%. Found: C 59.51%; H 8.17%; N 12.83%; S 9.82%.

EXAMPLE 3

3-(3,5-Di-tert.butyl-4-hydroxyphenyl)-6-hydroxymethyl-7H-thiazolo[3,2-b][1,2,4]triazin-7-one (a₁) 6-Hydroxymethyl-3-mercapto-2H-1,2,4-triazin-5-one

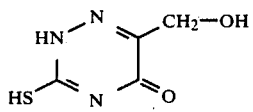

4.0 g (0.18 mol) of lithium borohydride were suspended in 100 ml of anhydrous tetrahydrofuran, and a solution of 19.0 g (0.094 mol) of 6-ethoxycarbonyl-3-mercapto-2H-1,2,4-triazin-5-one in 40 ml of absolute tetrahydrofuran was added dropwise while stirring and with ice cooling. The reaction mixture was then refluxed for 4 hours. After cooling, water was then added in portions with further stirring, and the mixture was adjusted to pH 1 using 10% strength sulfuric acid after the evolution of hydrogen was complete. After the tetrahydrofuran had been removed by evaporation under reduced pressure, the solution was extracted with ethyl acetate by means of a perforator. Evaporation of the organic phase, dried over sodium sulfate, and recrystallization of the solid residue from water gave the product in the form of yellow needles. Yield: 9.5 g (63% of theory). Melting point: 233°–235° C. $C_4H_5N_3O_2S$ (MW=159.2).

($a_2$) 3-(3,5-Di-tert.butyl-4-hydroxyphenyl)-6-hydroxymethyl-7H-thiazolo[3,2-b][1,2,4]triazin-7-one

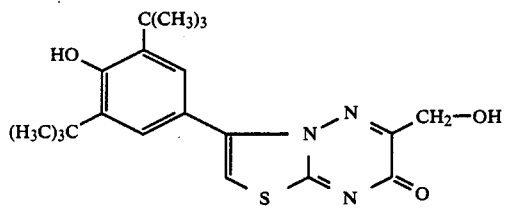

14.4 g (0.044 mol) of 2-bromo-1-(3,5-di-tert.butyl-4-hydroxyphenyl)-ethanone (Example 1$a_1$) and 7.0 g (0.044 mol) of 6-hydroxymethyl-3-mercapto-2H-1,2,4-triazin-5-one from step ($a_1$) were heated to boiling for 4 hours in 300 ml of ethanol. The reaction mixture, evaporated under reduced pressure, was dissolved in 300 ml of chloroform and treated with 100 ml of saturated sodium hydrogen carbonate solution. The chloroform phase was finally separated off, dried and evaporated. Chromatography of the crude product over silica gel using ethyl acetate/methanol (99:1) as eluent gave colorless needles.

Yield: 11.1 g (65% of theory). Melting point: 215°–217° C. $C_{20}H_{25}N_3O_3S$ (MW=387.5).

Analysis: Calculated: C 61.99%; H 6.50%; N 10.84%; S 8.27%. Found: C 61.98%; H 6.65%; N 10.75%; S 8.25%.

EXAMPLE 4

3-(3,5-Di-tert.butyl-4-hydroxyphenyl)-6-pyrrolidinomethyl-7H-thiazolo[3,2-b][1,2,4]triazin-7-one hydrochloride (by procedure d)

($d_1$) 3-(3,5-Di-tert.butyl-4-hydroxyphenyl)-6-chloromethyl-7H-thiazolo[3,2-b][1,2,4]triazin-7-one

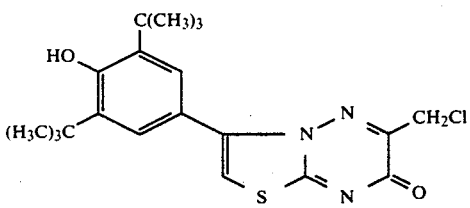

9.5 g (0.025 mol) of the thiazolo triazinone of the abovementioned Example 3$a_2$ were dissolved in 230 ml of dry methylene chloride and, after addition of 2.1 ml of pyridine, 7.0 g (0.06 mol) of thionyl chloride were added dropwise. After the mixture had been refluxed for 1 hour and cooled to room temperature, 200 ml of diethyl.ether were added and the mixture was allowed to stand overnight in a refrigerator. The crystals which precipitated out were filtered off under suction and dried in vacuo.

Yield: 6.7 g (66% theory). Melting point: 238°–240° C. $C_{20}H_{24}ClN_3O_2S$ (MW=405.9).

($d_2$) 3-(3,5-Di-tert.butyl-4-hydroxyphenyl)-6-pyrrolidinomethyl-7H-thiazolo[3,2-b][1,2,4]triazin-7-one hydrochloride

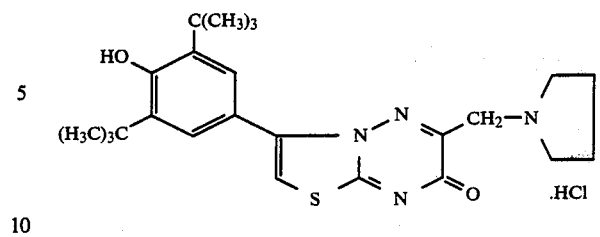

A solution of 6.7 g (0.017 mol) of the chloromethyl compound from step ($d_1$) in 100 ml of methylene chloride was heated to boiling for 2.5 hours after addition of 2.5 g (0.035 mol) of pyrrolidine, the mixture was then cooled, washed twice with water and dried over sodium sulfate, and an equimolar amount of ethanolic hydrochloric acid was added in order to form the hydrochloride. The crude product, produced in crystalline form, was filtered off and recrystallized from an isopropanol/ethyl acetate mixture (1:1).

Yield: 4.2 g (52% of theory). Melting point: 222°–223° l C. $C_{24}H_{33}ClN_4O_2S$ (MW=477.1).

Analysis: Calculated: C 60.42%; H 6.97%; Cl 7.43%; N 11.74%; S 6.72%. Found: C 60.46%; H. 7.25%; Cl 7.24%; N 11.49%; S 6.45%.

EXAMPLE 5

3-(3,5-Di-tert.butyl-4-hydroxyphenyl)-2,6-dimethyl-7H-thiazolo[3,2-b][1,2,4]triazin-7-one ($a_1$) 2-Bromo-1-(3,5-di-tert.butyl-4-hydroxyphenyl)-propanone

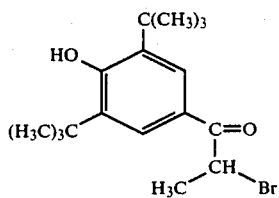

A solution of 82.0 g (0.31 mol) of 1-(3,5-di-tert.butyl-4-hydroxyphenyl)-propanone in 300 ml of chloroform was added dropwise while stirring to a boiling suspension of 139.0 g (0.62 mol) of copper(II) bromide in 300 ml of ethyl acetate. The mixture was subsequently refluxed for 3 hours until the evolution of hydrogen bromide was complete. After the mixture had been cooled to room temperature, the copper salts were filtered off under suction, the filter residue was washed twice with ethyl acetate, and the filtrate was evaporated under reduced pressure. The solid residue was recrystallized from petroleum ether (40°–60° C.).

Yield: 87.5 g (82% of theory). Melting point: 130°–132° C. $C_{17}H_{25}BrO_2$ (MW=341.3).

($a_2$) 3-(3,5-Di-tert.butyl-4-hydroxyphenyl)-2,6-dimethyl-7H-thiazolo[3,2-b][1,2,4]trizain-7-one

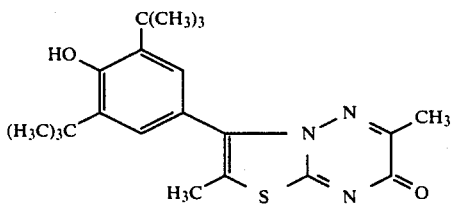

17.1 g (0.05 mol) of 2-bromo-1-(3,5-di-tert.butyl-4-hydroxyphenyl)-propanone from step (a₁) and 7.2 g (0.05 mol) of 3-mercapto-6-methyl-2H-1,2,4-triazin-5-one were stirred for 4 hours at 90° C. in 60 ml of glacial acetic acid. The reaction mixture, evaporated under reduced pressure, was dissolved in 300 ml of chloroform and treated with 100 ml of saturated sodium hydrogen carbonate solution. After the chloroform phase had been separated off, dried and evaporated, the solid was recrystallized twice from isopropanol.

Yield: 10.8 g (56% of theory). Melting point: 256°–257° C. $C_{21}H_{27}N_3O_2S$ (MW = 385.5).

Analysis: Calculated: C 65.42%; H 7.06%; N 10.90%; S 8.32%. Found: C 65.11%; H 7.15%; N 10.75%; S 8.16%.

EXAMPLE 12

3-(3-Aminomethyl-5-tert.butyl-4-hydroxyphenyl)-7H-thiazolo[3,2-b][1,2,4]triazin-7-one hydrochloride (by procedure (e))

(e₁) 3-(3-Tert.butyl-4-hydroxyphenyl)-7H-thiazolo[3,2-b][1,2,4]triazin-7-one hydrobromide

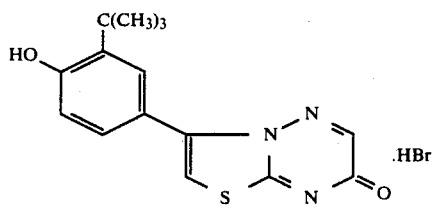

In accordance with procedure (a₂), 47.5 g (0.175 mol) of 2-bromo-1-(3-tert.butyl-4-hydroxyphenyl)-ethanone and 20.6 g (0.16 mol) of 3-mercapto-2H-1,2,4-triazin-5-one in 190 ml of glacial acetic acid were stirred at 90° C. for 1 hour. The precipitate formed on cooling was filtered off under suction and recrystallized from a mixture of ethyl acetate/ethanol.

Yield: 44.0 g (72% of theory). Melting point: 250°–252° C. (decomp.). $C_{15}H_{16}BrN_3O_2S$ (MW = 382.3).

Analysis: Calculated: C 47.13%; H 4.22%; Br 20.89%; N 10.98%; S 8.36%. Found: C 47.22%; H 4.25%; Br 20.43%; N 11.17%; S 8.60%.

(e₂) 3-(3-Aminomethyl-5-tert.butyl-4-hydroxyphenyl)-7H-thiazolo[3,2-b][1,2,4]triazin-7-one hydrochloride

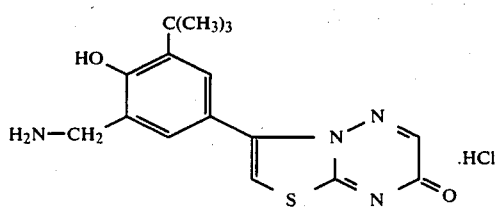

7.1 g (0.005 mol) of 2,2,2-trifluoro-N-(hydroxymethyl)acetamide were added in portions to a solution, cooled to 5° C., of 15.1 g (0.05 mol) of 3-(3-tert.butyl-4-hydroxyphenyl)-7H-thiazolo[3,2-b][1,2,4]triazin-7-one in 240 ml of methanesulfonic acid, and the mixture was subsequently stirred at room temperature for a further 3 hours. The reaction mixture was subsequently stirred into 1 liter of ice water and the batch of crystals was filtered off under suction.

In order to remove the trifluoroacetyl group, the N-acylated aminomethyl compound obtained was refluxed for 1 hour in 600 ml of 6N hydrochloric acid. The solution containing hydrochloric acid was filtered while hot, the filtrate was evaporated to dryness and the residue was fractionally recrystallized from ethyl acetate/methanol.

Yield: 8.4 g (46% of theory). Melting point: 210°–212° C. $C_{16}H_{19}ClN_4O_2S$ (MW = 366.9).

Analysis: Calculated: C 52.38%; H 5.22%, Cl 9.66%; N 15.27%; S 8.74%. Found: C 51.55%; H 5.40%; Cl 9.17%; N 14.98%; S 8.54%.

EXAMPLE 13

3-(3-Dimethylaminomethyl-5-tert.butyl-4-hydroxyphenyl)-7H-thiazolo[3,2-b][1,2,4]triazin-7-one hydrochloride (by procedure (e))

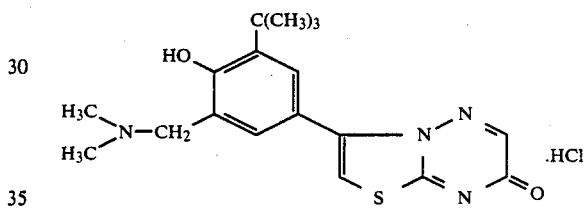

12.8 ml (0.28 mol) of a 40% strength aqueous dimethylamine solution were added dropwise with ice cooling to 6.4 ml (0.086 mol) of a 37% strength aqueous formaldehyde solution. After 4.2 g (0.011 mol) of 3-(3-tert.butyl-4-hydroxyphenyl)-7H-thiazolo[3,2-b][1,2,4]triazin-7-one hydrobromide from Example 12, step (e₁), and 70 ml of ethanol had been added, the mixture was heated to boiling for 19 hours. After cooling, 2N sodium hydroxide solution was added dropwise until the Mannich base precipitated out. The latter was filtered off under suction, an equimolar amount of ethanolic hydrochloric acid was added in order to form the hydrochloride, and the latter was finally recrystallized from water.

Yield: 3.0 g (69% of theory). Melting point: 260°–261° C. $C_{18}H_{23}ClN_4O_2S$ (MW = 394.9).

Analysis: Calculated: C 54.75%; H 5.87%; Cl 8.98%; N 14.19%; S 8.12%. Found: C 54.58%; H 5.89%; Cl 9.22%; N 13.90%; S 8.11%.

TABLE 1

Compounds of the formula I (see Claim 1)

| Example | R¹ | R² | R³ | Melting point °C. |
|---|---|---|---|---|
| 1 | (H₃C)₃C— | H | H | 257 (decomp.) |
| 2 | H₃C— | H | H | 225–226 (decomp.) |
| 3 | (H₃C)₃C— | H | —CH₂—OH | 215–217 |

TABLE 1-continued

| Example | R$^1$ | R$^2$ | R$^3$ | Melting point °C. |
|---|---|---|---|---|
| 4 | $(H_3C)_3C-$ | H | $-CH_2-N\langle\text{(pyrrolidine ring)}$ | 222–223 (as hydrochloride) |
| 5 | $(H_3C)_3C-$ | $-CH_3$ | $-CH_3$ | 256–257 |
| 6 | $(H_3C)_3C-$ | H | $-CH_3$ | 219–220 |
| 7 | $(H_3C)_3C-$ | $-CH_3$ | H | 249–251 |
| 8 | $(H_3C)_3C-$ | H | $-CH_2-CH_3$ | 240–242 |
| 9 | $(H_3C)_3C-$ | H | $-CH_2-CH_2-CH_3$ | 216–217 |
| 10 | $(H_3C)_3C-$ | H | $-CH(CH_3)_2$ | 237–238 |
| 11 | $H_3C-$ | H | $-CH_3$ | 232–233 |
| 12 | $H_2N-CH_2-$ | H | H | 210–212 (as hydrochloride) |
| 13 | $(H_3C)_3N-CH_2-$ | H | H | 260–261 (as hydrochloride) |
| 14 | $(H_5C_2)_2N-CH_2-$ | H | H | 234–236 (as hydrochloride) |
| 15 | (pyrrolidin-1-yl)$-CH_2-$ | H | H | 238–240 (as hydrochloride) |
| 16 | $-CH_2-N$(morpholine ring, $-CH_2-CH_2-O-CH_2-CH_2-$) | H | H | 177–179 (as hydrochloride) |

PHARMACOLOGICAL TESTING AND RESULTS

The compounds of the formula I according to the invention were tested for antiphlogistic action, influence on immunopathological processes, oxygen radical-deactivating potency, ulcerogenic activity and acute toxicity in the animal models described below, the antiphlogistic naproxen (2-(6-methoxy-2-naphthyl)-propionic acid), which is one of the first choice standard preparations in rheumatherapy, being included in the investigations as the comparison substance.

1. Adjuvant arthritis

The investigations were carried out by the method of Pearson (Arthrit. Rheum. 2 (1959) p. 44). The experimental animals used were male rats of a Wistar-Lewis strain having a body weight between 130 and 200 g. The compounds to be tested were administered orally (p.o.) once daily from day 1 to day 5 of the experiment in doses of 50 mg per kg of body weight. The animals of a control group received only the vehicle. Each preparation and control group comprised 8 animals. The criterion used to determine an action was the percentage reduction in the increase in paw volume compared to that of the untreated control group.

2. Acute gastral ulcerogenity

The investigation took place in each case on 10 male Sprague-Dawley rats in which the gastric mucous membrane had been sensitized by hunger stress. The body weight of the animals was between 200 and 300 g. While allowing free access to the drinking water, the feed was withdrawn 48 hours before administration of the test preparations until sacrifice of the animals. The rats were sacrificed 24 hours after oral administration of the substance, and the stomachs were removed, cleaned under running water and inspected for mucous membrane lesions. All macroscopically visible lesions were regarded as ulcers. The number of animals having ulcers was determined for each dose, and the UD$_{50}$ values, i.e. the doses at which lesions were caused in 50% of the animals, were calculated from this number by the method of Litchfield and Wilcoxon (J. Pharmacol. Exp. Ther. 96 (1949) p. 99).

3. Acute toxicity

The LD$_{50}$ values were determined by a standard method from the mortality occurring within 7 days in NMRI (Naval Medical Research Institute) mice (6 animals per dose) after a single intraperitoneal (i.p.) administration.

The results of these investigations, which clearly confirm the superiority of the compounds of the formula I according to the invention over the standard preparation naproxen, are collated in Table 2 below.

TABLE 2

| | Antiphlogistic action, ulcerogenity and acute toxicity | | |
|---|---|---|---|
| Compound from Example | Adjuvant arthritis (% inhibition at 50 mg/kg p.o.) | Acute ulcerogenicity UD$_{50}$ (mg/kg) | Acute toxicity LD$_{50}$ (mg/kg) |
| 1 | 67 | >400* | >1200 |
| 2 | 41 | >400* | >1200 |
| 3 | 41 | >200* | >1200 |
| 6 | 50 | >200* | >1200 |
| 9 | 45 | >200* | >1200 |
| Naproxen | 55 | 23 | 500 |

$^1$in each case the maximum dose administered

The dose/action curve in the model of adjuvant arthritis gave, for example for the compound from Example 1, an ED$_{50}$ value of 10.9 mg/kg, which is clearly more favorable than the corresponding comparison value of 17.5 mg/kg for the standard preparation naproxen. Applied to the acute ulcerogenity, dividing UD$_{50}$ by ED$_{50}$ gave a therapeutic range of >36.7 for the compound of Example 1, this range being only 1.3 for the comparison preparation naproxen, which underlines particularly impressively the great importance attached to the extremely good gastral tolerance of the compounds according to the invention. A likewise clear superiority over the comparison compound arises when the calculation of the therapeutic range is based on the $LD_{50}$ values determined, and the quotient $LD_{50}/ED_{50}$ is formed, which is greater than 110 for the compound of Example 1 and 28.6 for naproxen.

The compounds according to the invention also proved to be clearly superior to the standard preparation naproxen in further specific experiments.

4. Inhibition of immunopathological processes

It is today generally accepted that the advanced course of inflammatory rheumatic disorders is caused mainly by disfunctions in the immune system and that causal therapy can only succeed using medicaments which are capable of inhibiting these immunopathological processes.

(a) Adjuvant arthritis

In the rat model, described under point 1, of arthritis induced by Freund's adjuvant, the immune activity of lymphocytes towards certain mitogens, such as concavalin A, phytohemagglutinin A and dextran sulfate, is usually drastically reduced. The stimulating action on this greatly suppressed immune response was therefore investigated. In this investigation, the compounds from Example 1, for example, caused substantial normalization of the immune reactivity after oral administration of 3.15 and 6.3 mg/kg, whereas naproxen, which was tested in doses up to 25 mg/kg, was ineffective.

(b) Arthritis induced by type II collagen

In this experiment, arthritis was induced in male Wistar rats using type II collagen, which was obtained by standard methods of Miller and Rhodes (Meth. Enzymol. 82 (1982) p. 33) from the nasal septum of the calf and, mixed with Freund's incomplete adjuvant, was injected intradermally into the animals. This immunization process was repeated 7 days later. 20 days after the initial immunization, the affected rats were divided into groups each comprising 7 animals, which received the particular test substance or the pure vehicle (control group) orally once daily in the subsequent 20-day treatment phase. On day 41 of the experiment, i.e. one day after the final administration of substance, the increase in volume of both rear paws was determined.

In this experiment, the compound of Example 1, for example, exhibited a dose-dependent inhibition of the increase in paw volume, which was statistically significant from doses of 25 mg/kg p.o., while only non-significant inhibition values were produced for naproxen at the same dosage.

The immune status of lymphocytes is also disturbed sensitively in this model of collagen arthritis. For this reason, lyphocytes were obtained from the spleen of the experimental animals and their immune activity towards mitogens investigated, it again being possible to detect dose-dependent curative effects on the greatly weakened immune system for the compounds according to the invention, whereas naproxen produced no effect. Thus, for example, the compounds from Example 1 completely normalized the immune function of both T and B lymphocytes at a dose of 12 mg/kg p.o.

(c) Active Arthus reaction

The experimental animals used were female and male Sprague-Dawley rats having a body weight between 80 and 100 g; they were injected subcutaneously into the tail root with 0.5 ml of an emulsion of pertussis vaccine and ovalbumin in paraffin oil. After two weeks, the rats were divided into groups of 8 animals each. The respective test substance or the pure vehicle (positive control) were administered orally 24 hours and one hour before induction of the Arthus reaction by injecting 0.1 ml of a 0.4% strength ovalbumin solution into the right rear paw. Sodium chloride solution was injected into the left paw. A group of non-sensitized animals (negative control) was likewise treated with ovalbumin in order to be able to exclude non-specific reactions to the protein. The measurement parameter used for the action of the preparation was the inhibition of the increase in paw volume compared to that of a sensitized, but untreated control group (positive control) 4 hours after ovalbumin provocation, when the swelling reaches its maximum.

Non-steroidal antiphlogistics, including naproxen, are ineffective in this experimental set-up. By contrast, it was possible to impressively inhibit the Arthus reaction after oral administration of, for example, the compound of Example 1 having an $ED_{50}$ between 10 and 15 mg/kg.

5. Anti-oxidative action

According to current opinion, aggressive oxygen radicals, which are formed to excess during the chronic inflammation process and, as highly toxic inflammation mediators themselves, perpetually maintain the connective tissue destruction which proceeds via an irreversible lipid peroxidation of the cell membranes, are permanently involved in the progressive course, caused by a multitude of factors, of rheumatoid arthritis and other inflammatory disorders. As a result, antioxidatively active pharmaceuticals having the ability to deactivate these extremely cytotoxic oxygen radicals should permit specific engagement in the chronic course of the inflammation. A suitable animal model for this type of tissue destruction caused by oxygen radicals is Adriamycin (doxorubicin) induced inflammation in rats.

(a) Adriamycin-induced inflammation

The investigations were carried out by the method of D. M. Siegel et al. (Inflammation 4 (1980) p. 233) on male Sprague-Dawley rats having a body weight between 200 and 230 g in groups of 7 animals each, which received 0.1 mg of Adriamycin, dissolved in 0.1 ml of a 0.9% strength sodium chloride solution, by subcutaneous injection into the left rear paw. The increase in paw volume was determined by plethysmographic measurement 72 hours thereafter as a measure of the degree of inflammation.

The test preparations were administered orally in 1% strength aqueous carboxymethylcellulose suspension once daily on 4 successive days, starting with the day of Adriamycin injection.

As can be seen from Table 3, the compound from Example 1, for example, exhibited a strong, dose-dependent protective effect in this test against tissue destruction induced by Adriamycin. Both steroidal and non-steroidal antiphlogistics, including naproxen, are ineffective in this experimental set-up.

TABLE 3

| | Inhibition of Adriamycin-induced inflammation | | |
|---|---|---|---|
| Animal group | Dose in mg/kg p.o. | Increase in paw volume in μl | Protective action in % |
| Control | — | 430 | |
| Compound from Example 1 | 20 | 220 | 49* |
| | 40 | 200 | 54* |
| | 80 | 10 | 98* |

*Significance $p < 0.05$ (b) In-vitro inhibition of lipid peroxidation

Further convincing evidence of the pronounced protective action of the compounds according to the invention against aggressive oxygen radicals is provided by the thiobarbituric acid test of A. Ottolenghi (Arch. Biochem. Biophys. 79 (1959) pp. 355-363). Using this in-vitro method, the affect on microsomal and mitochondrial lipid peroxidation by antioxidatively active preparations can be determined from the malonodialdehyde produced on oxidative degradation of membrane-bound, polyunsaturated fatty acids.

Here too, the compounds of the formula I exerted a strong inhibitory action. For the compound of Example 1, for example, IC$_{50}$ values of $6 \times 10^{-7}$ and $3 \times 10^{-6}$ mol/l were produced using microsomes and mitochondria respectively from the rat liver.

6. Inhibition of 5-lipoxygenase

The inhibitory action of the compounds according to the invention on 5-lipoxygenase-catalysed degradation of arachidonic acid was investigated, as usual, in in-vitro experiments on isolated polymorphonuclear human granulocytes. To this purpose, cells stimulated by calcium ionophor A 23 187 (Calbiochem GmbH, Frankfurt/Main, FRG, Biochemical and Immunochemical Catalog 1985, p. 284) were incubated with $^{14}$C-labeled arachidonic acid, and the major radioactive degradation products of arachidonic acid, 5-hydroxyeicosatetraenoic acid (5-HETE) and leukotriene 8$_4$ (LTB$_4$), which has a particularly strong proinflammatory action, formed after 15 minutes at 37° C. by biotransformation were determined quantitatively with the aid of a radio monitor after separation by high-pressure liquid chromatography (HPLC).

In this experiment set-up, the formation of both LTB$_4$ and 5-HETE, and accordingly the degradation of arachidonic acid via 5-lipoxygenase, was significantly inhibited by pre-incubating the granulocytes for 15 minutes with the compound of Example 1, for example, in the concentration range between $10^{-5}$ and $10^{-6}$ mol/l.

We claim:

1. A substituted 3-phenyl-7H-thiazolo[3,2-b][1,2,4]-triazin-7-one of the formula I

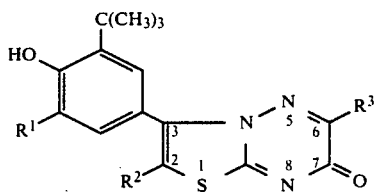

in which
R$^1$ is a straight-chain or branched alkyl group having 1 to 4 carbon atoms, hydroxymethyl or an aminomethyl group of the formula II

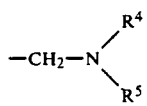

R$^2$ is a hydrogen atom or an alkyl radical having 1 to 3 carbon atoms, and
R$^3$ is a hydrogen atom, a straight-chain or branched alkyl group having 1 to 4 carbon atoms, hydroxymethyl or an aminomethyl group of the formula II, where
R$^4$ and R$^5$ are identical or different and are a hydrogen atom or a straight-chain or branched alkyl radical having 1 to 4 carbon atoms, or the two radicals, together with the nitrogen atom to which they are bound, form a heterocyclic ring selected from the group consisting of pyrrolidino, piperidino, hexamethyleneimino, morpholino, thiomorpholino, piperazino and homopiperazino, whereby said piperazino and homopiperazino rings can be alkylated on their second nitrogen atom with (C$_1$-C$_4$) alkyl, or a physiologically acceptable acid-addition salt of the compound having the structural element of the formula II in the positions of R$^1$ and/or R$^3$.

2. A compound as claimed in claim 1, wherein R$^1$ is a tert.butyl radical or an aminomethyl group of the formula II.

3. A compound as claimed in claim 1, wherein R$^1$ denotes a tert.butyl group and simultaneously R$^2$ and R$^3$, independently of one another, represent hydrogen or methyl.

4. A compound as claimed in claim 1, wherein R$^1$ is tert.butyl and R$^2$ and R$^3$ are hydrogen.

5. A compound as claimed in claim 1, wherein R$^2$ and R$^3$, independently of one another, are hydrogen or methyl.

6. A pharmaceutical composition comprising an amount effective for use in the therapy of a mammal of at least one compound of the formula I as claimed in claim 1 or a physiologically acceptable acid-addition salt of said compound having the structural element of the formula II as claimed in claim 1 in the position of at least one of R$^1$ and R$^3$, together with a pharmaceutically acceptable excipient.

7. A method for the prevention and treatment of disorders in which the therapeutic use of one or more of inflammation inhibitors, immune modulators, oxygen radical-deactivating agents and inhibitors of 5-lipoxygenase-induced degradation of arachidonic acid is indicated, which comprises administering an effective amount of a compound of the formula I as claimed in claim 1 or a physiologically acceptable acid-addition salt thereof.

8. A method as claimed in claim 7 for the prevention and treatment of inflammatory disorders.

9. A method as claimed in claim 8 for the prevention and treatment of inflammatory rheumatic disorders.

10. A method for the prevention and treatment of disorders in which the therapeutic use of one or more of inflammation inhibitors, immune modulators, oxygen radical-deactivating agents and inhibitors of 5-lipoxygenase-induced degradation of arachidonic acid is indicated, which comprises administering an effective amount of a pharmaceutical composition as claimed in claim 6.

11. A method as claimed in claim 10 for the prevention and treatment of inflammatory disorders.

12. A method as claimed in claim 10 for the prevention and treatment of inflammatory rheumatic disorders.

13. A method for the treatment of a patient suffering from an inflammatory disorder which comprises administering to said patient an effective amount for said treatment of at least one compound of the formula I as defined in claim 1, of at least one physiologically acceptable salt of said compound of the formula I having the structural element of the formula II in the position of at least one of R$^1$ and R$^3$, or of a mixture of said compound and said salt.

14. A method as claimed in claim 13 for the treatment of an inflammatory rheumatic disorder.

* * * * *